United States Patent
Shiobara et al.

(10) Patent No.: US 10,745,718 B2
(45) Date of Patent: Aug. 18, 2020

(54) MICROALGA HAVING AGGREGATION ABILITY

(71) Applicant: HONDA MOTOR CO., LTD., Tokyo (JP)

(72) Inventors: Nozomi Shiobara, Tochigi (JP); Shohei Kinoshita, Tochigi (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 16/309,220

(22) PCT Filed: Apr. 21, 2017

(86) PCT No.: PCT/JP2017/016099
§ 371 (c)(1),
(2) Date: Dec. 12, 2018

(87) PCT Pub. No.: WO2017/217116
PCT Pub. Date: Dec. 21, 2017

(65) Prior Publication Data
US 2019/0177747 A1    Jun. 13, 2019

(30) Foreign Application Priority Data
Jun. 17, 2016   (JP) .................................. 2016-120762

(51) Int. Cl.
C12P 7/06 (2006.01)
C12R 1/89 (2006.01)

(52) U.S. Cl.
CPC .................................... *C12P 7/06* (2013.01); *C12R 1/89* (2013.01); *Y02E 50/17* (2013.01); *Y02P 20/59* (2015.11)

(58) Field of Classification Search
CPC ..................... C12P 7/06; C12R 1/89
See application file for complete search history.

(56) References Cited

U.S. PATENT DOCUMENTS

2015/0353961 A1* 12/2015 Lee .................. C12P 7/16
435/160

FOREIGN PATENT DOCUMENTS

JP    07-087983    4/1995
JP    11-196885    7/1999

OTHER PUBLICATIONS

Lowder, Levi G., et al., "Heterologous expression of a Volvox cell adhesion molecule causes flocculation in Chlamydomonas reinhardtii", J. Appl. Phycol., 2015, vol. 27, pp. 721-731, see pp. 721-723, listed in International Search Report, English text, 11 pages.
He, Zhenzong, et al., "Influence of fractal-like aggregation on radiative properties of Chlamydomonas reinhardtii and H2 production rate in the plate photobioreactor", International Journal of Hydrogen Energy, 2015, vol. 40, pp. 9952-9965, see Abstract, pp. 9954-9955, English text, 14 pages.
Kong, Qing-xue, et al., "Culture of Microalgae Chlamydomonas reinhardtii in Wastewater for Biomass Feedstock Production", Appl. Biochem Biotechnol., 2010, vol. 160, pp. 9-18, see p. 11, p. 17, English text, 10 pages.
Liu, Weijie, et al., "Bioflocculant production from untreated corn stover using Cellulosimicrobium cellulans L804 isolate and its application to harvesting microalgae", Biotechnol. Biofuels, 2015, vol. 8:170, see Abstract, English text, 12 pages.
International Search Report, dated Jul. 25, 2017 (Jul. 25, 2017), 2 pages.

* cited by examiner

*Primary Examiner* — Ruth A Davis
(74) *Attorney, Agent, or Firm* — Rankin, Hill & Clark LLP

(57) ABSTRACT

In ethyl alcohol production using the self-fermentation of a microalga, a step of concentrating or collecting an algal body by centrifugal treatment, filtering treatment or the like is made unnecessary or simple to save labor for effort and equipment therefor is saved. The microalga belongs to *Chlamydomonas* sp., and is a variant strain which has an ability to produce ethyl alcohol under dark and anaerobic conditions and has acquired an ability to proliferate while aggregating. The microalga is proliferated and maintained under dark and anaerobic conditions to generate ethyl alcohol in this method for producing ethyl alcohol.

6 Claims, 12 Drawing Sheets

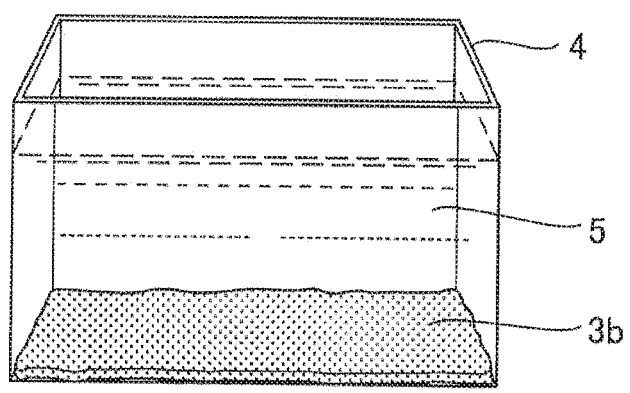

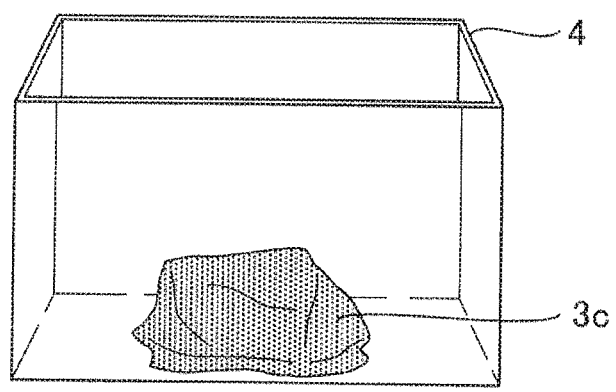

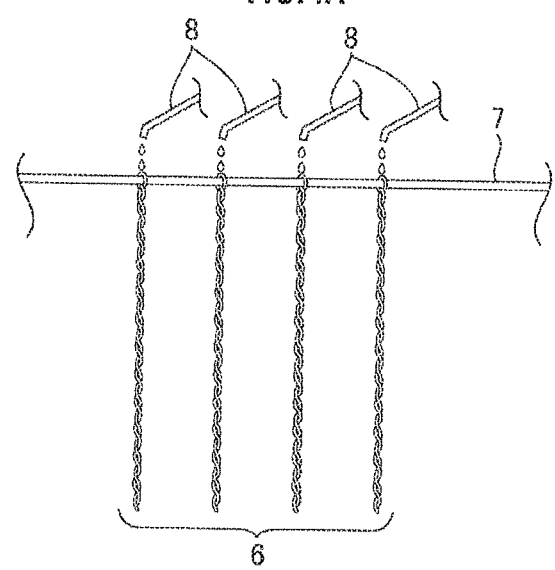

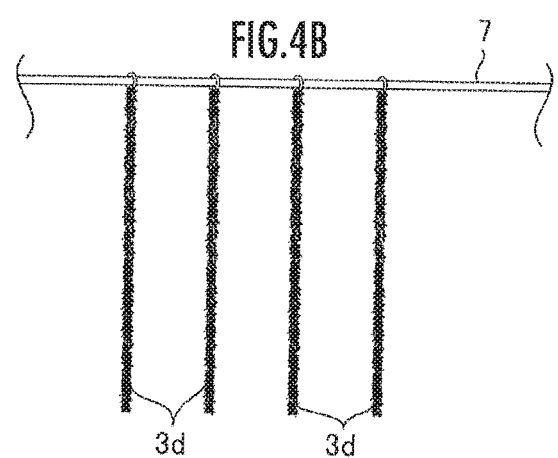

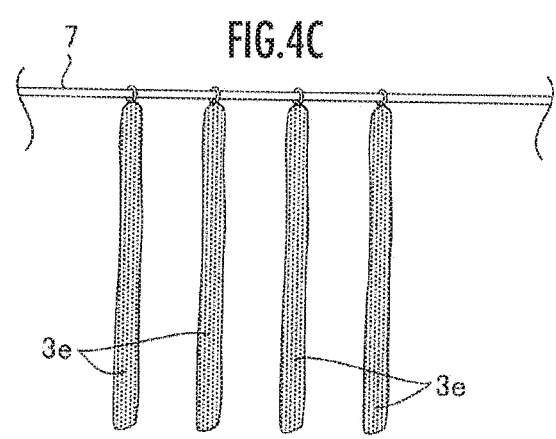

MICROALGA HAVING AGGREGATION ABILITY

TECHNICAL FIELD

The present invention relates to a microalga which contributes to the generation of renewable energy resources.

BACKGROUND ART

The development of biomass energy using renewable resources such as plants has been advanced as environmentally friendly energy resources replacing limited fossil fuel. For example, much starch is contained in edible portions of sugarcane, corn and the like, and high-purity ethyl alcohol, which can be used for automobile fuel or the like, can be comparatively efficiently produced from biomass thereof through steps such as saccharification, fermentation, distillation, purification. However, there is the problem of competition with food which mankind needs in biomass ethyl alcohol produced from food raw materials. When, the balance of $CO_2$ emission in steps such as saccharification, fermentation, distillation and refining is considered also as to the balance of the $CO_2$ emission for preventing warming, there has been the problem that it does not contribute so greatly.

Meanwhile, the development of technique for subjecting a microalga active in photosynthesis to self-fermentation to produce ethyl alcohol have also been advanced. According to this method, it is considered that sunlight energy can be converted efficiently, the steps of saccharification from starch and fermentation can be omitted, and it also contributes to an emission reduction in $CO_2$. There is no problem of competition with food, either.

For example, Patent Literature 1 discloses a method for producing ethyl alcohol from a microalga, wherein the method relates to the technique of the self-fermentation of a microalga, a microalga which accumulates starch in cells is cultivated, slurry obtained by concentrating a culture solution containing the cultivated algal body is maintained in the darkness and an anaerobic atmosphere with the pH maintained in the range of 6.0 to 9.0 to produce ethyl alcohol.

For example, Patent Literature 2 discloses a new microalga which relates to a technique of the microalga which can be cultivated without needing a large amount of fresh water, grows at a salt concentration of sea water and accumulates starch in cells; produces ethyl alcohol from starch in cells by maintaining it under dark and anaerobic conditions; and belongs to *Chlamydomonas* sp.

CITATION LIST

Patent Literature

Patent Literature 1: Japanese Patent No. 3004509
Patent Literature 2: Japanese Patent No. 3837589

SUMMARY OF INVENTION

Technical Problem

FIG. 7 schematically shows that a conventional microalga for producing ethyl alcohol is proliferated in a predetermined amount in a liquid medium. FIG. 8 shows a schematic process for producing ethyl alcohol by the self-fermentation of a conventional microalga for producing ethyl alcohol. As shown in FIG. 7, there are also many unicellular species which have swimming ability among conventional microalgae. Therefore, even though an algal body 11 proliferated in a liquid medium 5 which is contained in a container 4 is left to stand with container 4 the after proliferation, it is lacking in settleability, and remains almost dispersed. Therefore, as shown in FIG. 8, there has been the problem that a step of concentrating and collecting the algal body by centrifugal treatment, filtering treatment or the like is necessary and troublesome in a process of shifting from a proliferation system in which the microalga is proliferated to a self-fermentation system in which the proliferated algal body is exposed to the dark and an anaerobic atmosphere and subjected to self-fermentation, a process of removing the algal body exposed to the dark and an anaerobic atmosphere and shifting to a system in which ethyl alcohol is isolated, and the like, and costs are increased for effort and equipment therefor.

Then, an object of the present invention is, in ethyl alcohol production using the self-fermentation of a microalga, to make a step of concentrating or collecting an algal body by centrifugal treatment, filtering treatment or the like unnecessary or simple to save labor for effort and equipment therefor.

Solution to Problem

As a first aspect, the present invention provides a microalga belonging to *Chlamydomonas* sp., wherein the microalga is a variant strain which has an ability to produce ethyl alcohol under dark and anaerobic conditions and has acquired an ability to proliferate while aggregating to solve the above-mentioned problem.

Since this microalga is a variant strain which has an ability to produce ethyl alcohol under dark and anaerobic conditions and has acquired an ability to proliferate while aggregating, for example, when it is proliferated in a container containing a liquid medium, algal bodies proliferate while aggregating or algal bodies can be aggregated by spontaneous sedimentation after proliferation. The algal body aggregate can be easily separated from a proliferation system and shifted to a subsequent self-fermentation system (ethyl alcohol production system). It can be easily separated from a self-fermentation system (ethyl alcohol production system) and shifted to a subsequent ethyl alcohol isolation system. It can be efficiently proliferated by adhering the alga to a carrier such as threads and cloth and spraying a liquid medium, and the algal body aggregate in which algal bodies proliferate while aggregating on the carrier to form can be easily separated from a cultivation system and shifted to a subsequent self-fermentation system (ethyl alcohol production system). It can be easily separated from a self-fermentation system (ethyl alcohol production system) and shifted to a subsequent ethyl alcohol isolation system. Therefore, in ethyl alcohol production using the self-fermentation of a microalga, a step of concentrating or collecting an algal body by centrifugal treatment, filtering treatment or the like can be made unnecessary or simple to save labor for effort and equipment therefor. It is easy to reuse it for ethyl alcohol production or diverting it to other applications other than ethyl alcohol production.

In the microalga according to the present invention, the microalga is preferably a microalga belonging to *Chlamydomonas reinhardtii*.

Further, the microalga is preferably a Honda DREAMO strain (accession number FERM BP-22306).

Meanwhile, as a second aspect, the present invention provides a method for producing ethyl alcohol, wherein the above-mentioned microalga is proliferated and maintained under dark and anaerobic conditions to generate ethyl alcohol.

In the method for producing ethyl alcohol according to the present invention, it is preferable that the microalga is proliferated in a container containing a liquid medium to obtain an algal body aggregate in which algal bodies proliferate while aggregating or an algal body aggregate in which algal bodies are aggregated by spontaneous sedimentation after proliferation, and the algal body aggregate is maintained under dark and anaerobic conditions to generate ethyl alcohol.

Further, it is preferable that the microalga is proliferated with a liquid medium in contact with the microalga carried by a carrier to obtain an algal body aggregate in which algal bodies proliferate while aggregating on the carrier, and the algal body aggregate is maintained under dark and anaerobic conditions to generate ethyl alcohol.

Meanwhile, as a third aspect, the present invention provides a method for producing an algal body aggregate for producing ethyl alcohol, wherein the above-mentioned microalga is proliferated to obtain the algal body aggregate in which the algal bodies aggregate.

In the method for producing an algal body aggregate for producing ethyl alcohol according to the present invention, it is preferable that the microalga is proliferated in a container containing a liquid medium to obtain an algal body aggregate in which algal bodies proliferate while aggregating or an algal body aggregate in which algal bodies are aggregated by spontaneous sedimentation after proliferation.

Further, it is preferable that the microalga is proliferated with a liquid medium in contact with the microalga carried by a carrier to obtain the algal body aggregate in which algal bodies proliferate while aggregating on the carrier.

Meanwhile, as a fourth aspect, the present invention provides a method for producing ethyl alcohol, wherein the above-mentioned algal body aggregate is maintained under dark and anaerobic conditions to generate ethyl alcohol.

In the method for producing ethyl alcohol according to the present invention, it is preferable that accumulation of starch in cells of the alga is recovered, and then the algal body aggregate after the generation of ethyl alcohol is further maintained under dark and anaerobic conditions to generate ethyl alcohol.

Meanwhile, as a fifth side, the present invention provides the use of the algal body aggregate, wherein the algal body aggregate after the generation of ethyl alcohol in the above-mentioned method for producing ethyl alcohol is collected and used for applications other than ethyl alcohol production.

In the use of the algal body aggregate according to the present invention, the applications are preferably applications for blending in foods, medicines, quasi-drugs, health foods, functional foods, dietary supplements, supplements, medicines for animals and fish quasi-drugs for animals and fish, supplements for animals and fish, feeds for animals and fish, manure, and solid fuel.

Advantageous Effects of Invention

According to the present invention, in ethyl alcohol production using the self-fermentation of a microalga, a step of concentrating or collecting an algal body by centrifugal treatment, filtering treatment or the like can be made unnecessary or simple to save labor for effort and equipment therefor by using a variant strain which has acquired an ability to proliferate while aggregating.

BRIEF DESCRIPTION OF DRAWINGS

FIG. 3A, FIG. 3B and FIG. 3C show that a microalga is proliferated in a liquid medium in a predetermined amounts in one embodiment of the present invention, and FIG. 3A, FIG. 3B and FIG. 3C show states put in order of time after inoculation.

FIGS. 4A, 4B and 4C show that a microalga is proliferated on carriers in predetermined amounts in another embodiment of the present invention, and FIG. 4A, FIG. 4B and FIG. 4C show states put in order of time after inoculation.

DESCRIPTION OF EMBODIMENTS

Figure 1:
FIG. 1 shows a schematic process for producing ethyl alcohol by the self-fermentation of a microalga according to the present invention.

Examples of a microalga used for the present invention include a microalga belonging to *Chlamydomonas* sp., and more typically a microalga belonging to *Chlamydomonas reinhardtii*. This alga is accompanied with photosynthesis, and can grow, proliferate photoautotrophically and accumulate starch abundantly in cells by $CO_2$ fixation at that time. Meanwhile, it grows while oxidatively decomposing stored starch in the conditions that light and nutrition are short, it comes to produce ethyl alcohol further when it is exposed to the dark and an anaerobic atmosphere.

The microalga used for the present invention further needs the ability to proliferate while aggregating in addition to the above-mentioned ethyl alcohol production ability. As a microalga belonging to *Chlamydomonas* sp. and having such a characteristic, for example, a Honda DREAMO strain (accession number FERM BP-22306) and the like which are shown in the below-mentioned Examples are illustrated. However, it is not limited to this, and a variant strain having such character can be properly obtained at a practical frequency according to a request, for example, by performing as follows.

(Method for Obtaining Variant Strain)

It is cultivated in an environment which a parent strain does not like and which is obtained, for example, by setting conditions such as light, temperature, nutrition, $CO_2$, pH and dryness as unfavorable conditions, namely under the conditions that almost all the algal bodies become extinct, and a few surviving algal bodies appear while cultivation under the condition is repeated.

When there are survival algal bodies, they are collected. When a sure survival algal bodies are not obtained, the cultivation is performed under the same severe conditions again, and its cultivate is repeated until survival algal bodies appear.

A variant strain which has acquired the ability to proliferate while aggregating can be obtained by usually repeating exposure to a severe growth environment around tens to hundreds of times.

Examples of the environment which a parent strain does not like include a dark condition of 0 to 5 μmol/m²·sec, the dry condition of being almost dried-up, the condition that bacteria and the like proliferate markedly, the condition that a cold heat temperature cycle is very violently, the condition of the exhaustion of essential nutrient sources and combinations of any two or more of these. Variant strains which have acquired characteristics which is also suitable for cultivation outdoors such as the abilities to adapt to an environment in which it is grown only in a minimum amount of water and an environment in which it needs to survive for a long period of time even in the situation of photosynthesis being impossible together besides an environment in which it must grow while aggregating can be obtained by searching for variant strains which grow even under such severe conditions.

Maintenance such as the cultivation and the preservation of a microalga used for the present invention may be performed according to a well-known method conventionally used in a microalga belonging to Chlamydomonas sp., and is not particularly limited. That is, a liquid medium containing inorganic components such as nitrogen, phosphorus and potassium and other trace metallic elements components and an agar medium prepared by adding agar thereto are obtained. Cultivation is performed in the liquid medium or on the agar medium. Subculture is performed by transfer from preculture proliferated in a small amount of medium to a large amount of medium to increase the volume. Passage culture is performed at the same volume. Streak is performed on the agar medium, resulting in an increase to a predetermined amount, and preservation in a refrigerator is then performed. Such maintenance can be performed.

A light condition at the time of cultivation is preferably adjusted to around 5 to 1000 μmol/m²·sec by the irradiation of sunlight or artificial light, and more preferably to around 100 to 150 μmol/m²·sec. The temperature is preferably adjusted to around 5 to 40° C., and more preferably to around 20 to 30° C. The pH of a medium is preferably adjusted to around 5 to about 9, and more preferably to around 7. The subculture interval is preferably around 5 to 10 days at the time cultivation in a liquid medium at a volume of around 200 mL, and is preferably around 8 to 12 weeks at the time of cultivation on an agar medium. The rate of growth may be limited for long-term subculture, preservation on an agar medium or the like, and for that purpose, a light condition at the time of cultivation is preferably adjusted to around 0 to 150 μmol/m²·sec, and more preferably to around 5 to 20 μmol/m² sec and the temperature to 5 to 20° C. The preservation at 0° C. or less, or by freezing may result in death, and thus is not preferable.

Meanwhile, it is necessary to sufficiently proliferate a microalga and have starch stored in cells to produce ethyl alcohol at a sufficient yield. A light condition is preferably adjusted to around 5 to 1000 μmol/m²·sec, and more preferably to around 150 to 300 μmol/m²·sec by the irradiation of sunlight or artificial light for that purpose in addition to the above-mentioned conditions of maintenance or instead thereof as desirable conditions. The temperature is preferably adjusted to around 5 to 40° C., and more preferably to around 25 to 30° C. The pH of a medium is preferably adjusted to around 5 to 9, and more preferably to around 7.

The compositions of typical cultivation media are shown below. However, media are not limited to these media.

UREA Liquid Medium

| Solution A | 5.0 mL |
|---|---|
| Solution B | 5.0 mL |
| Solution C | 1.0 mL |

It is diluted to 1.0 L with distilled water and sterilized in an autoclave at 12° C. for 15 minutes.

TAP Liquid Medium

| Tris | 2.42 g |
|---|---|
| Solution B | 0.375 mL |
| Solution C | 1.0 mL |
| Solution D | 25 mL |
| Vinegar | 1.0 mL |

It is diluted to 1.0 liter with distilled water and sterilized in an autoclave at 121° C. for 15 minutes.

TAP Agar Medium
Agar is added to the TAP liquid medium (the amount of agar added 5.0 g/L).

Solution A

| $CH_4N_2O$ | 56.1 g |
|---|---|
| $MgSO_4 \cdot 7H_2O$ | 4.0 g |
| $CaCl_2 \cdot 2H_2O$ | 2.0 g |

It is diluted to 1.0 liter with distilled water.

Solution B

| $K_2HPO_4$ (anhydride) | 288.0 g |
|---|---|
| $KH_2PO_4$ | 144.0 g |

It is diluted to 1.0 liter with distilled water.

Solution C

| $ZnSO_4 \cdot 7H_2O$ | 22.0 g |
|---|---|
| $H_3BO_3$ | 11.4 g |
| $MnCl_2 \cdot 4H_2O$ | 5.06 g |
| $CoCl_2 \cdot 6H_2O$ | 1.61 g |
| $CuSO_4 \cdot 5H_2O$ | 1.57 g |
| $(NH_4)_6Mo_7O_{24} \cdot 4H_2O$ | 1.1 g |
| $FeSO_4 \cdot 7H_2O$ | 4.99 g |
| $C_{10}H_{16}N_2O_8$ (EDTA) | 50.0 g |

It is diluted to 1.0 liter with distilled water.

Solution D

| $NH_4Cl$ | 15.0 g |
|---|---|
| $MgSO_4 \cdot 7H_2O$ | 4.0 g |
| $CaCl_2 \cdot 2H_2O$ | 2.0 g |

It is diluted to 1.0 liter with distilled water.

The present invention will be described still more specifically hereinafter with reference to FIG.s. However, the present invention is not limited to these examples.

FIG. 1 shows a schematic process for producing ethyl alcohol by the self-fermentation of a microalga according to the present invention. As shown in this FIG., a step of concentrating or collecting an algal body by centrifugal treatment, filtering treatment or the like is made unnecessary or at least simple in a process of shifting from a proliferation system in which the microalga is proliferated to a self-fermentation system in which the proliferated algal body is exposed to the dark and an anaerobic atmosphere and subjected to self-fermentation, a process the algal body exposed to the dark and an anaerobic atmosphere is removed and shifting to an ethyl alcohol is isolation system in the present invention. It will be described still more specifically below.

Figure 2:
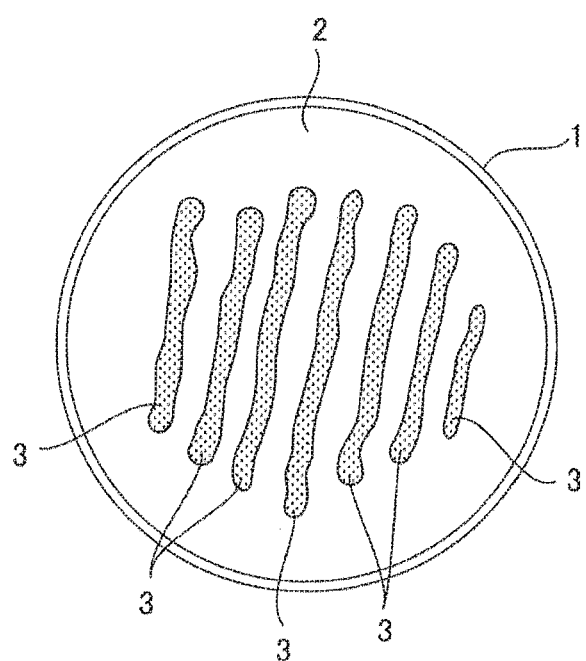
FIG. 2 shows that a microalga according to the present invention is proliferated on an agar medium in a predetermined amount.

FIG. 2 shows that a microalga according to the present invention is proliferated on an agar medium in a predetermined amount. That is, by streaking a proper amount of a preculture solution on agar medium 2 prepared in a petri dish 1 measuring 90 mm in diameter×20 mm in height with a sterilized platinum loop (it is so small an amount as not to be confirmed with the naked eye at this time) and leaving it to stand in the environment of a light intensity 5 to 20 $\mu mol/m^2 \cdot sec$ and 5 to 20° C., 1 to 3 weeks after the inoculation, a algal body becomes like algal bodies 3 in FIG. 2.

Figure 3A:
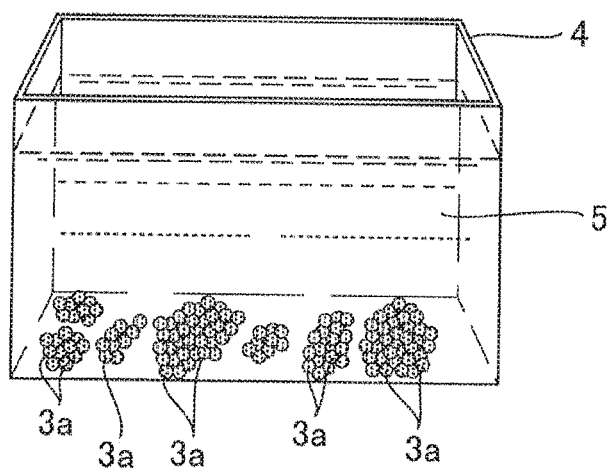

FIG. 3A, FIG. 3B and FIG. 3C show that a microalga is proliferated in a liquid medium in a predetermined amount in one embodiment of the present invention. That is, in this embodiment, a liquid medium 5 is prepared, and a container 4 having a capacity of 160 mL is charged therewith, some of the algal body proliferated on the above-mentioned agar medium is scratched and inoculated with a sterilized platinum loop, the liquid medium is stirred with the container to disperse the algal body directly after inoculation, the liquid medium is then left to stand in the environment of a light intensity of 100 to 150 $\mu mol/m^2 \cdot sec$ and 25 to 30° C., and 3 to 5 days after inoculation, the algal body thereby becomes like algal bodies 3a in FIG. 3A. Then, 5 to 7 days after inoculation, the algal body becomes like an algal body 3b in FIG. 3B. Further 7 to 10 days, the film of the algal body 3b at the bottom in FIG. 3B increases in thickness. When the container is shaken lightly horizontally in this state, the algal body becomes like an algal body 3c in FIG. 3C. FIG. 3C shows the algal body with the liquid medium removed. More specifically in FIG. 3A, a plurality of colonies of the algal body 3a gathering in the form of particles at a size of around 0.5 to 5 mm in the major axis, more typically around 1 to 2 mm are dispersed at the bottom of the container 4, and the colonies are dispersed while forming still larger masses. In FIG. 3B, the dispersed colonies of the algal body become still denser, and the algal body 3b proliferates like it covers almost all of the bottom to be membranous. In FIG. 3C, the algal body 3c which has increased in thickness is gathered in the shape of a carpet by stirring in the lateral direction.

Figure 7:
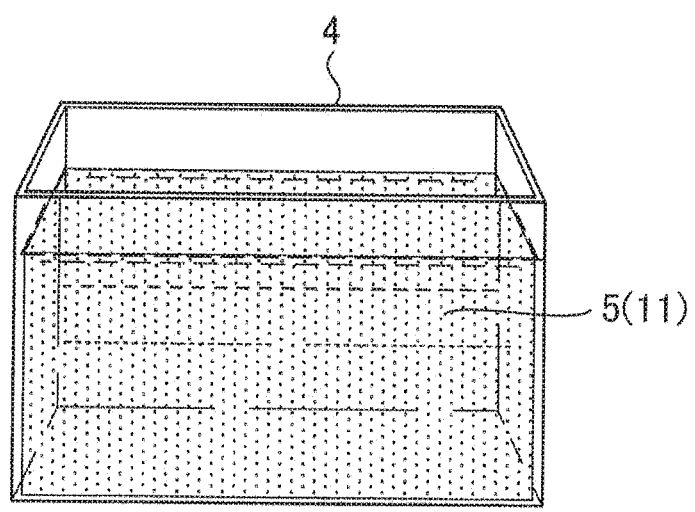
FIG. 7 shows that a conventional microalga for producing ethyl alcohol is proliferated in a liquid medium in a predetermined amount.
Figure 8:
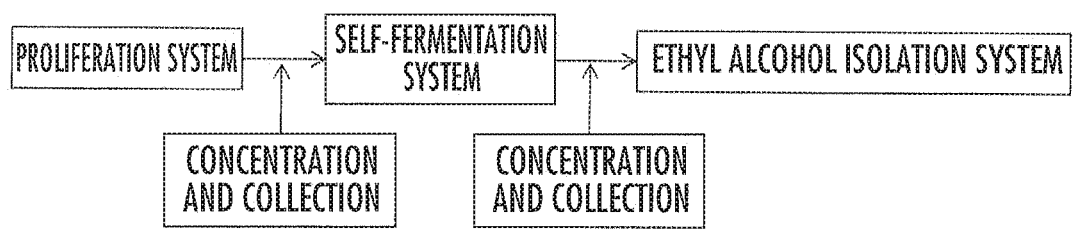
FIG. 8 shows a schematic process for producing ethyl alcohol by the self-fermentation of a conventional microalga for producing ethyl alcohol.

Thus, since the microalga according to the present invention has the ability to proliferate while aggregating, it is different from a conventional microalga shown in FIG. 7 in the point that the proliferated algal body forms an algal body aggregate by gathering itself. Therefore, the case thereof is different from the cases where conventional microalgae are used in the point that the algal body aggregate can be separated easily and shifted to subsequent steps in the present invention. "Separated easily" mentioned here means that the algal body aggregate can be separated from the liquid medium without being subjected to treatment of centrifugal separation or treatment with a filter and more specifically that the algal body aggregate can be separated from the liquid medium without being subjected to treatment of centrifugal separation or treatment with a filter (1), for example, by having such self-supportability that it can be picked by a hand or tongs and taken out of the container 4 and the liquid medium 5 in FIG. 3A, FIG. 3B and FIG. 3C or the like and (2), for example, by having such self-supportability that solid-liquid separation is possible by draining the liquid medium 5 from the container 4 in FIG. 3A, FIG. 3B and FIG. 3C with a pump or the like connected to a sucking port at a predetermined size, or the like.

The above-mentioned algal body aggregate may be formed during proliferation or by settling the alga by itself after proliferation in a predetermined amount. Therefore, for example, even when all or a part of the algal body is dispersed during proliferation and cannot be distinguished from a conventional type shown in FIG. 7 in appearance, such an algal body aggregate may be formed after proliferation in a predetermined amount, and the effect of the present invention can be enjoyed sufficiently. All the algal body does not need to form the algal body aggregate necessarily. When at least a part of the proliferated algal body can form such an algal body aggregate, the algal body aggregate can be shifted to a subsequent self-fermentation system (ethyl alcohol production) under dark and anaerobic conditions. Therefore, the effect of the present invention can be enjoyed sufficiently. For example, when 30% by wet mass or more out of the proliferated algal body can form such an algal body aggregate, it is preferable. When 50% by wet mass or more can form such an algal body aggregate, it is more preferable. When more than 70% by wet mass or more can form such an algal body aggregate, it is still more preferable. When 99% by wet mass or more can form such an algal body aggregate, it is the most preferable.

FIGS. 4A, 4B and 4C show that a microalga is proliferated on carriers in a predetermined amount in another embodiment of the present invention. That is, in this embodiment, a predetermined number of carriers 6 comprising threads are hung from a carrier retainer 7, and the microalga is carried by the carriers 6 and proliferated. FIG. 4A more specifically shows that a liquid medium in which the microalga is dispersed from liquid feeders 8 is dripped from above, and it is adhered to the carriers 6 comprising threads. A method for adhering the microalga to the carriers 6 is not particularly limited, and may be a method such as spraying the liquid medium in which the microalga is dispersed and adhering the microalga to the carriers 6; immersing the carriers 6 in the culture solution of the microalga; making the carriers 6 absorb the culture solution of the microalga; or the like. A dispersion liquid of the microalga may be a liquid which does not inhibit the growth of the microalga, while when a liquid medium suitable for the growth of a microalga is used as the liquid, water is absorbed in the carriers 6, or it adheres to the carriers 6; and this comes in contact with the microalga, and is used as nutrition in the early stage, and therefore it is more preferable. Then, 1 to 2 days after inoculation, the algal body becomes like algal bodies 3d in FIG. 4B by leaving it to stand in the environment of a light intensity 100 to 300 $\mu mol/m^2 \cdot sec$ and 10 to 30° C. Then, 5 to 7 days after inoculation, the algal body becomes like algal bodies 3e in FIG. 4C. It is preferable to maintain the algal body proliferating on the carriers 6 so that the algal body is not very dry during the proliferation of the microalga, and it is preferable to drip the liquid which does not inhibit the growth of the microalga from above along the carriers 6, spray it on the carriers 6, maintain humidity in the environmental atmosphere, or do the like if needed. When a liquid medium suitable for growth of the microalga is used as the liquid as above, water is absorbed in the carriers 6, or it adheres to the carriers 6; and this comes in contact with the microalga, and is used as additional nutrition, and therefore it is more preferable.

Thus, since the microalga according to the present invention has the ability to proliferate while aggregating, it is different from a conventional microalga shown in FIG. 7 in the point that it can be proliferated efficiently by adhering it to a carrier such as threads or cloth and spraying a liquid medium. That is, it is different in the point that the algal body aggregate in which algal bodies proliferate while aggregating on the carriers is formed. Therefore, the case thereof is different from the cases where conventional microalgae are used in the point that the algal body aggregate can be separated easily shifted to subsequent steps in the present invention. "Separated easily" mentioned here means that the algal body aggregate can be separated from the liquid medium without being subjected to treatment of centrifugal separation or treatment with a filter. This embodiment can be achieved by (1), for example, shifting the algal body aggregates formed on the carriers with the carriers to a self-fermentation system (ethyl alcohol production system) or a subsequent ethyl alcohol isolation system, or the like, or (2), for example, by scratching them from the carriers and then shifting them to a self-fermentation system (ethyl alcohol production system) or a subsequent ethyl alcohol isolation system, or the like.

Next, a step of generating ethyl alcohol will be described with reference to FIGS. 5 and 6.

Ethyl alcohol can be produced from the microalga, the algal bodies or the algal body aggregates obtained as above by the self-fermentation thereof by maintaining this under dark and anaerobic conditions according to a conventionally well-known method.

Figure 5:
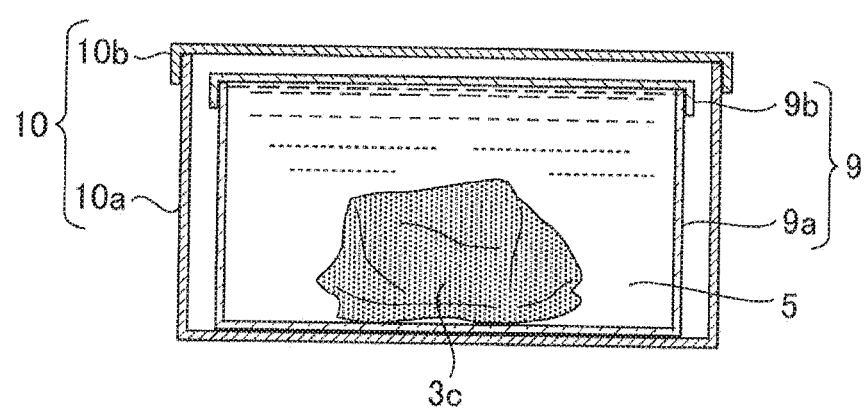
FIG. 5 shows that a microalga is proliferated in a liquid medium in a predetermined amount in one embodiment of the present invention and shifted to a self-fermentation system to generate ethyl alcohol.

For example, FIG. 5 shows an example using the algal body 3c described in the above-mentioned FIG. 3A, FIG. 3B and FIG. 3C. That is, the algal body 3c is taken out of the container 4 and stored in the storage part 9a of the airtight container 9, which is filled with a liquid medium 5 and closed airtightly with a lid 9b. The volume of the space in which the liquid is not contained on the basis of the amount of the liquid medium 5 ($CO_2$ and $O_2$ are present) is very small. This forms an anaerobic environment. When an airtight container is not used, a method for making inert gas such as $N_2$ gas or He gas flow and replacing air may be adopted. The whole airtight container 9 was stored in the storage part 10a of a black box 10 and closed airtightly with a lid 10b. This forms a dark condition. The dark condition may be formed by covering the airtight container 9 with aluminum foil or a blackout curtain, and the airtight container itself may have a light blocking effect. The amount of the liquid medium 5 on the basis of the algal body 3c, as expressed in the ratio of algal body 3c (g):liquid medium 5 (mL), is preferably 1:5, and more preferably 2:5. The temperature condition is preferably 5 to 45° C., and more preferably 25 to 35° C. The pH is preferably 5 to 9, and more preferably 7.0. It becomes a low-concentration ethyl alcohol solution at around 0.1 to 1% by volume by maintaining this environment for around 6 to 72 hours.

Figure 6:
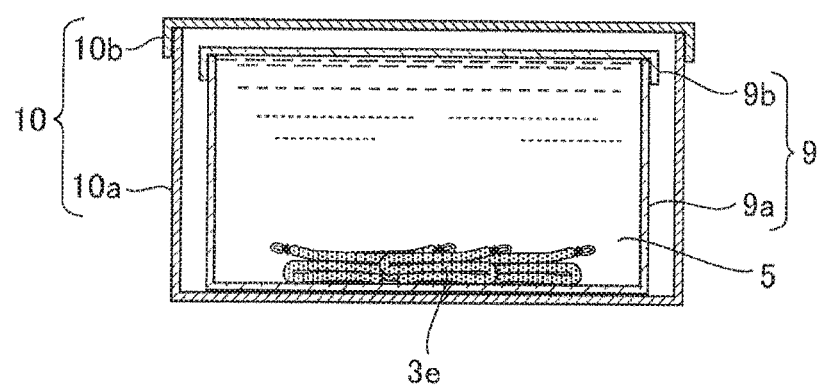
FIG. 6 shows that a microalga is proliferated on a carrier in a predetermined amount in another embodiment of the present invention and shifted to a self-fermentation system to generate ethyl alcohol.

Meanwhile, FIG. 6 shows an example using the algal bodies 3e described in the above-mentioned FIGS. 4A, 4B and 4C. That is, the algal body 3e is taken out of the container 4 with the carrier 6 comprising threads and stored in the storage part 9a of the airtight container 9, which is then filled with the liquid medium 5 and closed airtightly with the lid 9b. Others are the same as those of the aspect described in the above-mentioned FIG. 5. It becomes a low-concentration ethyl alcohol solution at around 0.1 to 1% by volume by maintaining this environment for around 6 to 72 hours.

Ethyl alcohol can be isolated from the low-concentration ethyl alcohol solution obtained as above according to a conventionally well-known method. For example, the low-concentration ethyl alcohol solution after self-fermentation can be passed through activated carbon, and ethyl alcohol can be selectively adsorbed on the inside of activated carbon. The ethyl alcohol concentration in the activated carbon, which is the purity, can be increased around 7 times more highly at a maximum than the concentration of the low-concentration ethyl alcohol after self-fermentation thereby. When a self-fermentation solution at an ethyl alcohol concentration of 0.5% by volume is used, around 3.5% concentrated liquid is obtained in activated carbon, and high-purity ethyl alcohol can be isolated by subjecting this activated carbon to distillation directly. Alternatively, the low-concentration ethyl alcohol solution after self-fermentation may be subjected to distillation without any treatment to isolate ethyl alcohol, or the purity of ethyl alcohol can also be increased in a method such as performing pervaporation using a hollow fiber membrane, an osmosis membrane or the like.

In another aspect of the present invention, an algal body aggregate used for ethyl alcohol production may be reused. That is, since the accumulation of starch in algal cells is usually exhausted or insufficient in the algal body aggregate used for ethyl alcohol production, the accumulation of starch is recovered, then it is further maintained under dark and anaerobic conditions as described above, and ethyl alcohol can be generated. To recover the accumulation of starch in algal cells, the recovery can be performed, for example, by maintaining the algal body aggregate collected from the self-fermentation system for predetermined time under a light condition, or the like. At that time, it is preferable to maintain the algal body aggregate wet, and it is more preferable to maintain the algal body aggregate while bring it in contact with a suitable culture medium used for maintenance such as cultivation and the preservation of a microalga. Further, it is preferable to maintain it in an aerobic environment where it can come in contact with $CO_2$ and $O_2$.

A light condition for recovering starch accumulation is preferably adjusted to around 5 to 1000 $\mu mol/m^2 \cdot sec$, and more preferably to around 100 to 150 $\mu mol/m^2 \cdot sec$ by the irradiation of sunlight or artificial light. The temperature is preferably adjusted to around 5 to 40° C., and more preferably to around 20 to 30° C. The pH of the culture medium is preferably adjusted to around 5 to 9, and more preferably to 7. The proliferation of the alga is not necessary for this starch accumulation recovery, and since the excessive growth of the alga leads to energy waste on the contrary, growth may be performed under the condition that the rate of growth is limited to some extent, and for that purpose, a light condition is preferably adjusted to around 0 to 150 $\mu mol/m^2 \cdot sec$, and more preferably to around 5 to 20 $\mu mol/m^2 \cdot sec$ and the temperature to 5 to 20° C.

In another aspect of the present invention, the algal body aggregate used for producing ethyl alcohol may be collected, and may be diverted to other applications other than ethyl alcohol production. That is, the algal body aggregate used for ethyl alcohol production usually contains nutritional components such as lipid and protein or energy supply components abundantly. Therefore, it is suitable as blending materials in various products and the like such as in foods, medicines, quasi-drugs, health foods, functional foods, dietary supplements, supplements, medicines for animals and fish, quasi-drugs for animals and fish, supplements for animals and fish, feeds for animals and fish, manure, and solid fuel. As the aspect of use, it is contained as a part of materials of these products and the like, and the amount thereof blended may be set properly depending on the type of products and the like, and is not particularly limited. For example, in the case of foods or feeds for animals or fish, it is preferable to blend 0.01 to 100% by mass of the algal body aggregate, and more preferable to blend 10 to 50% by mass on the basis of the whole. For example, in the case of medicines, quasi-drugs, medicines for animals or fish, or quasi-drugs for animals or fish, it is preferable to blend 0.01 to 50% by mass of the algal body aggregate, and more preferable to blend 1 to 30% by mass on the basis of the whole. For example, in the case of health foods, functional foods, dietary supplements, or supplements, it is preferable to blend 0.01 to 50% by mass of the algal body aggregate, and more preferable to blend 1 to 30% by mass on the basis of the whole. For example, in the case of manure, it is preferable to blend 0.01 to 100% by mass of the algal body aggregate, and more preferable to blend 10 to 50% by mass on the basis of the whole. For example, in the case of solid fuel, it is preferable to blend 0.01 to 100% by mass of the algal body aggregate, and more preferable to blend 10 to 50% by mass on the basis of the whole.

Needless to say, a method for producing ethyl alcohol using the microalga is not limited to the aspects described above, and can also be used suitably for other practical equipment and facilities in mass production methods.

EXAMPLE

Although the present invention will be described by Examples hereinafter still more specifically, the present invention is not limited to the scope of the following Example.

Test Example 1

A variant having the ability to proliferate while aggregating is probed using the following typical strain as a parent strain.
<Parent Strain>
 Place of origin: United States of America
 Separation source: *Chlamydomonas reinhardtii*
 Strain storage facilities: National Institute for Environmental Studies
 Strain number: NIES-2236
<Exposure to Severe Growth Environment>
The above-mentioned parent strain was cultivated in a UREA liquid medium and concentrated by centrifugal separation. A slurry algal body is further dried by air-drying to be almost dried-up. Then, a minute amount of the semidry algal body was rubbed at the center on the inside of the lid of a container having a capacity of IL, the lid and a light blocking effect. The container was charged with 800 mL of the UREA liquid medium, and the lid on which the algal body was rubbed was fastened. This container was closed completely airtightly and maintained in the dark at 20 to 25° C. for 5 days. The container was charged with the liquid at this time also to prevent the alga rubbed on the inside of the lid from drying completely by generating steam by evaporation. The container was stirred up and down after the maintenance for 5 days with the container closed airtightly, and the algal body rubbed on the inside of the lid was dropped into the liquid medium. The container was then maintained with the container maintained closed airtightly for further five days at 20 to 25° C. and around 200 µmol/m$^2$·sec under a light and dark cycle (8L16D: light 8 hours; dark 16 hours). After maintenance for 5 days, the container was opened, the culture solution was taken out, and the usual liquid cultivation was performed. It can be confirmed visually that green becomes deeper as cultivation days passes when there were survival strains. When any survival strain could not be confirmed, the above-mentioned cycle was performed again, and it was repeated until survival strain appeared.
<Aggregation Test>
Aggregation tests were performed as to the obtained survival strain. In the aggregation tests, usual liquid cultivation was performed in a cultivation bottle, and it was observed whether an algal body aggregated in the shape of a carpet when the bottle was shaken right and left with it proliferated until sediment of the algal body becomes thick.

Then, 51 strains were picked from strains in which aggregability was exhibited in the above-mentioned test among survival strains by FACS, the phototaxis method, the manipulation method, the antibiotic method and the like, and the usual agar cultivation was performed. Next, 24 strains growing excellently were selected from 51 cultivated strains, and bacteriological examinations and microscope observation were performed. In the bacteriological examination, a medium for bacterial proliferation (GPY liquid medium: 2% glucose, 1% poly peptone, 0.5% yeast extract) was used, 30 µL of the alga culture solution was mixed into 100 µL of the GPY liquid media, and the mixture was maintained at 28° C. in the dark for a maximum of 14 days. Whether the media were suspended or not was confirmed and whether bacteria grew or not was confirmed by microscope observation after the 7th day of the cultivation.

It was confirmed that 22 strains among the 24 strains were purified strains by bacteriological examinations. Additionally, it was determined from having the swimming ability, colors, forms and the like in microscope observation that 19 strains among the 22 strains were *Chlamydomonas* algae.

These selected 19 strains were subjected to agar cultivation, the strain which grew best was selected and deposited with International Organism Depository, National Institute of Technology and Evaluation (#120, 2-5-8 Kazusakamatari, Kisarazu-shi, Chiba) as a Honda DREAMO strain (accession date Apr. 22, 2016, accession number FERM BP-22306).

When the DNA nucleotide sequence (the rate of sequence determination: 85% or more of the entire genome) was investigated as to the Honda DREAMO strain separately, high homology exceeding 99.9% was shown as compared with the reference sequence of *Chlamydomonas reinhardtii* entered into the NCBI database. Therefore, it was determined that the Honda DREAMO strain is a microalga belonging to *Chlamydomonas* sp. and is further a microalga belonging to *Chlamydomonas reinhardtii*.

REFERENCE SIGNS LIST

1 petri dish
2 agar medium
3, 3*a*, 3*b*, 3*c*, 3*d* and 3*e* algal body
4 container
5 liquid medium
6 carrier
7 carrier retainer
8 liquid feeder
9 airtight container
9*a* storage part of airtight container 9b lid of airtight container
10 black box
10a storage part of black box
10b lid of black box
11 algal body

The invention claimed is:

1. A microalga belonging to *Chlamydomonas reinhardtii*, wherein the microalga is a variant strain of *Chlamydomonas reinhardtii*, which has an ability to produce ethyl alcohol under dark and anaerobic conditions and has an ability to proliferate while aggregating, wherein the variant strain of *Chlamydomonas reinhardtii* is acquired by a method comprising exposing *Chlamydomonas reinhardtii* to a growth environment comprising a combination of a dark condition of 0 to 5 $\mu mol/m^2 \cdot sec$ and at least one of a condition of exhaustion of essential nutrient sources and an air-tight condition, wherein the microalga is a Honda DREAMO strain (accession number FERM BP-22306) which has an ability to produce ethyl alcohol under dark and anaerobic conditions and to proliferate while aggregating.

2. A method for producing ethyl alcohol, wherein the microalga according to claim 1 is proliferated and maintained under dark and anaerobic conditions to generate ethyl alcohol.

3. The method for producing ethyl alcohol according to claim 2, wherein the microalga is proliferated in a container containing a liquid medium to obtain an algal body aggregate in which algal bodies proliferate while aggregating or an algal body aggregate in which algal bodies are aggregated by spontaneous sedimentation after proliferation, and the algal body aggregate is maintained under dark and anaerobic conditions to generate ethyl alcohol.

4. The method for producing ethyl alcohol according to claim 3, wherein accumulation of starch in cells of the alga is recovered, and then the algal body aggregate after the generation of ethyl alcohol is further maintained under dark and anaerobic conditions to generate ethyl alcohol.

5. The method for producing ethyl alcohol according to claim 2, wherein the microalga is proliferated with a liquid medium in contact with the microalga carried by a carrier to obtain an algal body aggregate in which algal bodies proliferate while aggregating on the carrier, and the algal body aggregate is maintained under dark and anaerobic conditions to generate ethyl alcohol.

6. The method for producing ethyl alcohol according to claim 5, wherein accumulation of starch in cells of the alga is recovered, and then the algal body aggregate after the generation of ethyl alcohol is further maintained under dark and anaerobic conditions to generate ethyl alcohol.

* * * * *